United States Patent [19]
Beck et al.

[11] Patent Number: 5,574,199
[45] Date of Patent: Nov. 12, 1996

[54] PARA-SELECTIVE AROMATIZATION PROCESS WITH EX SITU SELECTIVATED ZEOLITE CATALYST

[75] Inventors: Jeffrey S. Beck, Princeton; Ralph M. Dessau, Edison, both of N.J.

[73] Assignee: Mobil Oil Corporation, Fairfax, Va.

[21] Appl. No.: 372,467

[22] Filed: Jan. 13, 1995

Related U.S. Application Data

[63] Continuation-in-part of Ser. No. 69,251, May 28, 1993, Pat. No. 5,476,823.

[51] Int. Cl.$^6$ .................................................. C07C 15/00
[52] U.S. Cl. .................... 585/407; 585/400; 585/467; 585/475; 585/481
[58] Field of Search ........................... 585/400, 407, 585/467, 475, 481

[56] References Cited

U.S. PATENT DOCUMENTS

| | | |
|---|---|---|
| 3,698,157 | 10/1972 | Allen et al. . |
| 3,756,942 | 9/1973 | Cattanach . |
| 3,760,024 | 9/1973 | Cattanach . |
| 3,845,150 | 10/1974 | Yan et al. . |
| 4,016,218 | 4/1977 | Haag et al. . |
| 4,060,568 | 11/1977 | Rodewald . |
| 4,090,981 | 5/1978 | Rodewald . |
| 4,100,215 | 7/1978 | Chen . |
| 4,117,026 | 9/1978 | Haag et al. . |
| 4,127,616 | 11/1978 | Rodewald . |
| 4,145,315 | 3/1979 | Rodewald . |
| 4,175,057 | 11/1979 | Davies et al. . |
| 4,180,689 | 12/1979 | Davies et al. . |
| 4,283,306 | 8/1981 | Herkes . |
| 4,326,994 | 4/1982 | Haag et al. . |
| 4,379,761 | 4/1983 | Olson et al. . |
| 4,465,886 | 8/1984 | Rodewald . |
| 4,477,583 | 10/1984 | Rodewald . |
| 4,548,914 | 10/1985 | Chu . |
| 4,590,321 | 5/1986 | Chu . |
| 4,927,979 | 5/1990 | Yamagishi et al. . |
| 4,950,835 | 8/1990 | Wang et al. . |
| 5,019,263 | 5/1991 | Haag et al. . |
| 5,173,461 | 12/1992 | Absil et al. . |
| 5,476,823 | 12/1995 | Beck et al. ............................. 502/60 |

FOREIGN PATENT DOCUMENTS

0296582A2  12/1986  European Pat. Off. .

OTHER PUBLICATIONS

Nakajima et al. "p–Xylene–selective Disproportionation of Toluene over a Modified pentasil Type Zeolite", *Sekivu Gakkaishi*, 35; 185–189 (1992).

Chen et al. "M2 Forming–A Process for Aromatization of Light Hydrocarbons", *Ind. Eng. Chem. Process Des. Dev.*, 25; 151–155 (1986).

Hibino et al. "Shape–Selectivity over HZSM–5 Modified by Chemical Vapor Deposition of Silicon Alkoxide", *Journal of Catalysis*, 128; 551–558 (1991).

*Primary Examiner*—Asok Pal
*Attorney, Agent, or Firm*—Ronald A. Bleeker; Malcolm D. Keen; Peter W. Roberts

[57] ABSTRACT

A process for shape selective hydrocarbon aromatization that involves contacting a hydrocarbon feedstream, under aromatization conditions, with a catalytic molecular sieve which has been modified by being ex situ selectivated with a silicon compound. The ex situ selectivation involves exposing the catalytic molecular sieve to at least two selectivation sequences, each sequence comprising contacting the catalytic molecular sieve with a silicon compound followed by calcination. Optionally, the modified catalytic molecular sieve may be further selectivated in situ.

21 Claims, 1 Drawing Sheet

FIG. 1

PARA-SELECTIVE AROMATIZATION PROCESS WITH EX SITU SELECTIVATED ZEOLITE CATALYST

CROSS-REFERENCE TO RELATED APPLICATIONS

This is a continuation-in-part of co-pending application Ser. No. 08/069,251 filed on May 28, 1993 now U.S. Pat. No. 5,476,823. The entire disclosure of the above-cited application is expressly incorporated herein by reference.

BACKGROUND OF THE INVENTION

The present invention is directed to an improved process of shape selective conversion of hydrocarbons to aromatic compounds over a modified catalytic molecular sieve.

The term "shape-selective catalysis" describes unexpected catalytic selectivities in zeolites. The principles behind shape selective catalysis have been reviewed extensively, e.g., by Chen et al, "Shape Selective Catalysis in Industrial Applications," 36, Marcel Dekker, Inc. (1989). Within a zeolite pore, hydrocarbon conversion reactions such as paraffin isomerization, olefin skeletal or double bond isomerization, oligomerization and aromatic disproportionation, alkylation or transalkylation reactions are governed by constraints imposed by the channel size. Several principal shape selectivity constraints operate in zeolite catalyzed reactions. Reactant selectivity occurs when a fraction of the feedstock is too large to enter the zeolite pores to react. Product selectivity, on the other hand, occurs when some of the products of the reaction cannot leave the zeolite channels. Product distributions can also be altered by transition state selectivity in which certain reactions cannot occur because the reaction transition state is too large to form within the zeolite pores or cages. Another type of selectivity results from configurational constraints on diffusion where the dimensions of the molecule approach that of the zeolite pore system. A small change in the dimensions of the molecule or the zeolite pore can result in large diffusion changes leading to different product distributions. This type of shape selective catalysis is demonstrated, for example, in selective hydrocarbon aromatizations.

It is well known to convert saturated hydrocarbons to aromatic compounds by means of zeolite catalysts. Such a process is described in U.S. Pat. No. 3,756,942. The catalyst disclosed in this patent for producing aromatic compounds in high yield is a ZSM-5 type zeolite. These catalysts are described as suitable for selectively promoting the conversion of hydrocarbons such as paraffins, olefins, and naphthenes to aromatic compounds. Yields of 30 wt.% and more of aromatic compounds based on the non-aromatic portion of the hydrocarbon feedstock were reported in this patent.

Another such process is described in U.S. Pat. No. 3,760,024. This patent describes processes converting $C_2$–$C_4$ paraffins and/or olefins to $C_6$–$C_{10}$ aromatics over ZSM-5 type catalysts.

Another process is described in U.S. Pat. No. 4,180,689. This process involves a gallium-based HZSM-5 catalyst for conversion of light hydrocarbons into benzene, toluene and xylene (BTX) and hydrogen. This process, however, demonstrates little if any enhanced shape selectivity, producing xylenes generally at or near equilibrium, with the para-isomer around 24% of total xylenes. In addition, this process produces significant quantities of high-boiling $C_9$+ aromatics, amounting to greater than 8% of the total amount of aromatics formed.

Other processes are described in U.S. Pat. Nos. 4,590,321 and 3,845,150. U.S. Pat. No. 4,590,321 describes conversions of non-aromatic compounds such as smaller paraffins and/or olefins to aromatic compounds over ZSM-5 type catalysts modified with phosphorus oxide. U.S. Pat. No. 3,845,150 describes processes for heat balancing in conversions of mixtures of paraffins and olefins to aromatics over ZSM-5 type catalysts. Other such processes are disclosed in U.S. Pat. Nos. 5,019,263, 4,326,994, and 4,117,026. Other types of processes are disclosed in Chen et al., Ind. Eng, Chem, Proc. Des. Dev., 25, 151-155 (1986), and U.S. Pat. Nos. 4,175,057 and 4,180,689.

Various methods are known in the art for increasing the para-selectivity of zeolite catalysts. One such method is to modify the catalyst by treatment with a "selectivating agent". For example, U.S. Pat. Nos. 5,173,461, 4,950,835, 4,927,979, 4,465,886, 4,477,583, 4,379,761, 4,145,315, 4,127,616, 4,100,215, 4,090,981, 4,060,568 and 3,698,157 disclose specific methods for contacting a catalyst with a selectivating agent containing silicon ("silicon compound").

Other types of selectivating agents are known. For example, U.S. Pat. No. 4,548,914 describes another modification method involving impregnating catalysts with oxides that are difficult to reduce, such as those of magnesium, calcium, and/or phosphorus, followed by treatment with water vapor to improve para-selectivity. European Patent No. 296,582 describes the modification of aluminosilicate catalysts by impregnating such catalysts with phosphorus-containing compounds and further modifying these catalysts by incorporating metals such as manganese, cobalt, silicon and Group IIA elements. The patent also describes the modification of zeolites with silicon compounds. U.S. Pat. No. 4,950,321 also describes modification of catalysts with phosphorus compounds.

Traditionally, ex situ selectivation of zeolites has involved single applications of the selectivating agent. It may be noted, however, that a suggestion of multiple treatments was made in U.S. Pat. No. 4,283,306 to Herkes. The Herkes patent discloses an attempt to promote crystalline silica catalyst by application of an amorphous silica such as ethylorthosilicate. The Herkes disclosure shows that a twice-treated catalyst is less selective than a once-treated catalyst, as measured by methylation of toluene by methanol, indicating that multiple ex situ selectivation confers no benefit and in fact reduces a catalyst's efficacy in this reaction.

Various organic compounds have been employed as carriers for selectivating agents in the impregnation methods applied to zeolite catalysts. For example, U.S. Pat. Nos. 4,145,315, 4,127,616, 4,090,981 and 4,060,568 describe the use of inter alia $C_5$–$C_7$ alkanes as solvents for impregnation of zeolites with selectivating agents containing silicon. There has been no suggestion, however, of the use of lower volatility alkanes as carriers for impregnation of zeolites.

Therefore, it would be a significant advance in the art to overcome the above-described difficulties, disadvantages and deficiencies associated with conventional shape selective hydrocarbon aromatization processes in a manner that would enable use of modified catalytic sieves produced by methods which are both more efficient and safer and that would also increase product yields and reduce the proportion of undesirable impurities in the product of such aromatization processes.

The present invention solves the difficulties, disadvantages, and deficiencies inherent in the prior art by providing an improved process for shape selective hydrocarbon aromatization. The process of the invention produces higher rates of conversion of hydrocarbons to aromatic compounds, greater product selectivity, and greater product purity than do conventional processes.

Accordingly, it is a purpose of the invention to provide an improved process for the shape selective conversion of hydrocarbon compounds to aromatic compounds.

It is a further purpose of the invention to provide an improved process for converting hydrocarbons to aromatic compounds which overcomes the above-described difficulties, disadvantages, and deficiencies of the prior art practice of these processes.

Other purposes and advantages of the present invention will be more fully apparent from the following detailed disclosure and appended claims.

SUMMARY OF THE INVENTION

In one aspect, the invention is a process of shape selective hydrocarbon aromatization over a modified catalytic molecular sieve by contacting a reaction stream comprising olefins and/or paraffins, under aromatization conditions, with a modified catalytic molecular sieve. The modified catalytic molecular sieve is prepared by a modification method which includes exposing the catalytic molecular sieve to at least two ex situ selectivation sequences. Each ex situ selectivation sequence includes a step of contacting the catalytic molecular sieve with a selectivating agent, followed by a step of calcining the contacted catalytic molecular sieve. Selectivating agents useful in the present invention include a large variety of silicon-containing compounds, preferably silicon polymers which are soluble in organic carriers. Such organic carriers include various alkanes, preferably paraffins having 7 or more carbons.

In a further embodiment, the invention also includes a process of shape selective hydrocarbon aromatization over a modified catalytic molecular sieve that has been further modified by in situ trim-selectivating the modified catalytic molecular sieve. The in Situ trim-selectivating may be performed by coke trim-selectivating wherein an organic compound is decomposed in the presence of the modified catalytic molecular sieve, at conditions suitable for decomposing the organic compound. Alternatively, the trim-selectivating may be performed by exposing the modified catalytic molecular sieve to a reaction stream that includes a hydrocarbon to be converted and a selectivating agent selected from a group of compounds including a large variety of silicon-containing compounds, at reaction conditions.

Advantageously, the described modified catalysts possess enhanced shape selectivity for hydrocarbon aromatization. Accordingly, the aromatization process of the invention exhibits increased selectivity for para-xylene.

For a better understanding of the present invention, together with other and further purposes, reference is made to the following description as well as the accompanying drawing, the scope of which will be pointed out in the appended claims.

DETAILED DESCRIPTION OF THE INVENTION

The present invention relates to enhanced shape selective processes for the conversion of hydrocarbons to aromatic compounds over modified catalytic molecular sieves. In particular, the invention relates to the shape selective aromatization of low molecular weight olefins and paraffins to commercially useful para-xylene.

The catalytic molecular sieves useful according to the invention preferably include intermediate pore zeolites. It is preferred that, prior to selectivation, the catalytic molecular sieves exhibit a Constraint Index of between about 1 and about 12. The method for determining Constraint Index is described fully in U.S. Pat. No. 4,016,218, the disclosure of which is incorporated by reference herein. Zeolites which conform to the specified values of Constraint Index for intermediate pore zeolites include, for example, ZSM-5, ZSM-11, ZSM-5/ZSM-11 intermediate, ZSM-12, ZSM-22, ZSM-23, ZSM-35, ZSM-48, ZSM-50, and ZSM-57. An especially preferred zeolite is ZSM-5. Such zeolites are described, for example, in U.S. Pat. Nos. 3,702,886 and U.S. Pat. Redesign No. 29,949, U.S. Pat. Nos. 3,709,979, 3,832, 449, 4,046,859, 4,556,447, 4,076,842, 4,016,245, 4,229,424, 4,397,827, 4,640,849, 4,046,685, 3,308,069 and U.S. Pat. Redesing No. 28,341, to which reference is made for the details of these zeolites.

The catalytic molecular sieves useful for the invention are preferably in the hydrogen, "as-synthesized", form prior to modification, but may be used in the ammonium or sodium form. Other materials may also be present, including hydrogen precursor, organic cations, and combinations thereof. "Hydrogen precursor" compounds include compounds well known in the art, such as quaternary nitrogen compounds, which contain hydrogen substituents, and which, upon heating generate protons. Hydrogen precursor compounds are described, for example, in U.S. Pat. No. 3,755,483 to Burgess, the disclosure of which is incorporated by reference herein.

The crystal size of zeolites used for the invention is preferably greater than about 0.1 micron. The accurate measurement of crystal size of zeolite materials is frequently very difficult. Microscopy methods, such SEM and TEM, are often used, but these methods require measurements on a large number of crystals and for each crystal measured, values may be required in up to three dimensions. For ZSM-5 materials described in the examples below, estimates were made of the effective average crystal size by measuring the rate of sorption of 2,2-dimethylbutane at 90° C. and 60 torr hydrocarbon pressure. The crystal size is computed by applying the diffusion equation given by J. Crank, *The Mathematics of Diffusion*, Oxford at the Clarendon Press, 52–56 (1957), for the rate of sorbate uptake by a solid whose diffusion properties can be approximated by a plane sheet model. In addition, the diffusion constant of 2,2-dimethylbutane, D, under theses conditions is taken to be $1.5 \times 10^{-14}$ cm$^2$/ sec. The relation between crystal size measured in microns, d, and diffusion time measured in minutes, $t_{0.3}$, the time required for the uptake of 30% of capacity of hydrocarbon, is:

$$d = 0.0704 \times t_{0.3}^{1/2}.$$

In the present case, these measurements have been made on a computer controlled, thermogravimetric electrobalance, but there are numerous ways one skilled in the art could obtain the data.

The "alpha value" of a catalyst is an approximate indication of the catalytic cracking activity of the catalyst compared to a standard catalyst, and it gives the relative rate constant (rate of normal hexane conversion per volume of catalyst per unit time). It is based on the activity of the amorphous silica-alumina cracking catalyst taken as an alpha of 1 (Rate Constant =0.016 sec$^{-1}$). The alpha test is described in U.S. Pat. No. 3,354,078 and in *Journal of Catalysis*, 4, 522–529 (1965); 2, 278 (1966); 61, 395 (1980), each incorporated herein by reference as to that description. It is noted that intrinsic rate constants for many acid-catalyzed reactions are proportional to the alpha value for a particular crystalline silicate catalyst (see "The Active Site of Acidic Aluminosilicate Catalysts", *Nature*, 309, 589–591 (14 Jun. 1984). The experimental conditions of the test used herein include a constant temperature of 538° C. and a variable flow rate as described in detail in the *Journal of Catalysis*, 61, 395 (1980). The catalyst in the present invention preferably has an alpha value greater than 1, for example, from about 1 to about 2000. More preferably the alpha value of the catalyst is in the range of from about 1 to about 100. The alpha value of the catalyst may be increased by initially treating the catalyst with nitric acid or by mild steaming before preselectivation. This type of steaming is discussed in U.S. Pat. No. 4,326,994.

The silica to alumina ratio ($SiO_2/Al_2O_3$) of the catalysts of the invention may be determined by conventional analysis. This ratio is meant to represent, as closely as possible, the ratio in the rigid atomic framework of the zeolite crystal and to exclude aluminum in the binder or in cationic or other form within the channels. Although zeolites with a silica to alumina ratio of up to about 10,000 are useful, it is preferred to use zeolites having ratios of at least about 20 to about 500.

For the improved aromatization processes of this invention, the suitable molecular sieve may be employed in combination with a support or binder material such as, for example, a porous inorganic oxide support or a clay binder. While the preferred binder is silica, other non-acidic binder materials may be employed, generally in the form of dried inorganic oxide gels or gelatinous precipitates. Suitable clay materials include, by way of example, bentonite and kieselguhr. The relative proportion of suitable crystalline molecular sieve to the total composition of catalyst and binder or support may be from about 10% to about 98% by weight and is preferably from about 50% to about 80% by weight of the composition. The composition may be in the form of an extrudate, beads or fluidizable microspheres.

The catalyst to be modified may also include a hydrogenation/dehydrogenation function such as added metal selected from Groups IB to VIII of the Periodic Table. These metals include, for example, platinum, palladium, nickel, copper, cobalt, gallium, molybdenum, rhodium, ruthenium, silver, gold, mercury, osmium, iron, zinc, cadmium, and mixtures thereof, may be utilized. Preferred metals include gallium, zinc and platinum. The most preferred metal is gallium. The metal may be added in amounts of from about 0.001% to about 2%, typically about 0.5% to about 1% by weight of the catalyst. The metals may be incorporated in the aromatization catalyst by methods known in the art, such as impregnation, ion exchange, and physical mixing. The metal and the catalyst may also be co-crystallized by adding the metal to the catalyst crystallization mixture. For example, a platinum-modified catalyst can be prepared by first adding the catalyst to a solution of ammonium nitrate in order to convert the catalyst to the ammonium form. The catalyst is subsequently contacted with an aqueous solution of tetraamine platinum (II) nitrate or tetraamine platinum (II) chloride. The catalyst can then be filtered, washed with water and calcined at temperatures of from about 250° C. to about 500° C.

The metal incorporated into the catalyst is preferably in the form of its oxide. An important advantage of the present invention is the stability of the oxide in the presence of the oxidant, which is usually air. The oxidant prevents conversion of the metal oxide, such as zinc and gallium oxides, to the free metal, which is more susceptible to begin eluted from the catalyst than the metal oxide.

In conventional applications, the silicon compound employed may be in the form of a solution, an emulsion, a liquid or a gas under the conditions of contact with a zeolite. For the modification of catalysts according to the invention the silicon compound is preferably contacted with the catalyst as a liquid, more preferably as a solution including a silicon-containing selectivating agent dissolved in an organic carrier. The deposited silicon compound extensively covers, and resides substantially exclusively on, the external surface of the molecular sieve. Examples of methods of depositing silicon on the surface of the zeolite are found in U.S. Pat. Nos. 4,090,981, 4,127,616, 4,465,886 and 4,477,583, which are incorporated by reference herein. Further examples of the deposition of a silicon compound on zeolite surfaces are described in Nakajima et al., *Sekiyu Gakkaishi*, 35, 185–189 (1992), and in U.S. Pat. No. 4,950,835.

For the modification method of the present invention, a zeolite, either incorporated with a binder or in unbound form, is contacted at least twice, preferably between about two and about six times, with a selectivating agent dissolved in an organic solvent/carrier. The selectivating agent comprises a compound or polymer containing a main group or transition metal, preferably silicon. The catalyst is contacted with a solution of the silicon-containing selectivating agent in an organic solvent at a catalyst/selectivating agent weight ratio of from about 100/1 to about 1/100, at a temperature of from about 10° C. to about 150° C., at a pressure of from about 0 psig to about 200 psig, for a time of from about 0.1 hr to about 24 hours. The organic carrier is preferably removed, e.g., by distillation, or evaporation with or without vacuum. The catalyst is then calcined. This methodological sequence comprising a step of contacting the catalyst with the selectivating agent and a step of calcining the contacted catalyst is termed a "selectivation sequence." The catalysts of the invention, then, are exposed to at least two of these selectivation sequences.

As used herein, the term "selectivating agent" is used to indicate substances which will increase the shape-selectivity of a catalytic molecular sieve to the desired levels while maintaining commercially acceptable levels of hydrocarbon conversion. Such substances include, for example, organic silicon compounds such as phenylmethyl silicone, dimethyl silicone, and blends thereof which have been found to be suitable. In general, such organosilicon compounds must be soluble in organic solvents such as those described elsewhere herein. In addition, a "solution" is intended to mean a uniformly dispersed mixture of one or more substances at a molecular or ionic level. The skilled artisan will appreciate that solutions, both ideal and colloidal, differ from emulsions.

Useful selectivating agents include silicones and silicone polymers which can be characterized by the general formula:

wherein $R_1$ and $R_2$ are independently selected from among hydrogen, halogen, hydroxyl, alkyl, halogenated alkyl, aryl, halogenated aryl, aralkyl, halogenated aralkyl, alkaryl or halogenated alkaryl. The hydrocarbon substituents generally contain from 1 to 10 carbon atoms, preferably methyl or ethyl groups. Also in the general formula, n is an integer of at least 2 and generally in the range of 3 to 1000. The molecular weight of the silicone compound employed is generally between about 80 and about 20,000 and preferably within the approximate range of 150 to 10,000. Representative silicone compounds include dimethyl silicone, diethyl silicone, phenylmethyl silicone, methylhydrogen silicone, ethylhydrogen silicone, phenylhydrogen silicone, methylethyl silicone, phenylethyl silicone, diphenyl silicone, methyltrifluoropropyl silicone, ethyltrifluoropropyl silicone, polydimethyl silicone, tetrachloro-phenylmethyl silicone, tetrachlorophenylethyl silicone, tetrachlorophenylhydrogen silicone, tetrachlorophenylphenyl silicone, methylvinyl silicone and ethylvinyl silicone. The silicone compound need not be linear, but may be cyclic, for example, hexamethyl cyclotrisiloxane, octamethyl cyclo-tetrasiloxane, hexaphenyl cyclotrisiloxane and octaphenyl cyclotetrasiloxane. Mixtures of these compounds may also be used, as may silicones with other functional groups.

Other silicon compounds, including silanes and alkoxysilanes, such as tetramethoxy silane, may also be utilized. These useful silicon-containing selectivating agents include silanes and alkoxysilanes characterizable by the general formula:

where $R_3$, $R_4$, $R_5$ and $R_6$ are independently selected from the group consisting of hydrogen, hydroxyl, halogen, alkyl, halogenated alkyl, alkoxy, aryl, halogenated aryl, aralkyl, halogenated aralkyl, alkaryl, and halogenated alkaryl groups. Mixtures of these compounds may also be used.

Preferred silicon-containing selectivating agents include dimethylphenylmethyl polysiloxane (e.g., Dow-550) and phenylmethyl polysiloxane (e.g., Dow-710). Dow-550 and Dow-710 are available from Dow Chemical Co., Midland, Mich.

Preferably, the kinetic diameter of the high efficiency, selectivating agent is larger than the zeolite pore diameter, in order to avoid entry of the selectivating agent into the pore and any concomitant reduction in the internal activity of the catalyst.

Examples of suitable organic solvents or organic carriers for the organosilicon selectivating agent include linear, branched, and cyclic alkanes having three (3) or more carbons. In the catalyst modification methods of the present invention, it is preferred that the solvent or carrier be a linear, branched, or cyclic alkane having a boiling point greater than about 70° C., and most preferably containing 7 or more carbons. Optionally, mixtures of low volatility organic compounds, such as hydrocracker recycle oil, may be employed as solvents. Especially preferred low volatility hydrocarbon solvents of selectivating agents include decane and dodecane.

It has been found that a multiple selectivation scheme provides increased efficiency of deposition of the silicon compound on the surface of the catalyst. This is especially true when the catalyst is employed in combination with a binder, as described elsewhere herein, prior to selectivation. This increased efficiency allows for the use of relatively small quantities of the silicon compound as well as relatively small quantities of the solvent. Accordingly, the amount of silica deposited on the catalyst, as a fraction of the silicon compound in the selectivating agent solution, tends to be greater when the deposition is performed stepwise in a sequential fashion according to the invention, than when the deposition is made entirely by a single impregnation of the catalyst. In addition, it has been observed that the selectivity of the catalysts modified by multiple selectivation sequences tends to be substantially higher than the selectivity of a catalyst modified by the deposition of a comparable amount of silica in a single step.

Following each contacting of the catalyst with a selectivating agent, wherein the silicon compound is deposited, the contacted catalyst is calcined to decompose the molecular or polymeric species to a solid state species. The catalyst may be calcined by increasing the temperature at a rate of from about 0.2° C./minute to about 5° C./minute, until reaching a temperature greater than 200 C., but below a temperature at which the crystallinity of the zeolite is adversely affected. Generally, such temperature will be below 600° C. Preferably the temperature of calcination is within the approximate range of 350° C. to 550 C. The product is maintained at the calcination temperature usually for 1 to 24 hours, preferably for between 2 and 6 hours.

The calcination process may be performed in an atmosphere of $N_2$, an oxygen-containing atmosphere, preferably air, an atmosphere of $N_2$ followed by an oxygen-containing atmosphere, or an atmosphere containing a mixture of $N_2$ and air. Calcination should be performed in an atmosphere substantially free of water vapor, to avoid undesirable uncontrolled steaming of the silicon coated catalyst. The catalyst may be calcined once or more than once after each silicon deposition. The various calcinations in any impregnation sequence need not be identical, but may vary with respect to the temperature, the rate of temperature rise, the atmosphere and the duration of calcination.

Factors upon which the amount of silica incorporated with the zeolite is dependent include temperature of contact with the selectivating agent, the type and concentration of the silicon compound in the contacting medium, the degree to which the zeolite has been dried prior to contact with the silicon compound, the conditions of calcination of the contacted zeolite, and the number of selectivation sequences performed.

Subsequent to the ex situ selectivation of the catalyst, the catalyst may be further modified in situ, i.e., in the reactor in which the hydrocarbon conversion process of the invention is performed. The hydrocarbon feed may be co-fed simultaneously with a second silicon-containing selectivating agent and hydrogen at reaction conditions until the desired p-dialkylbenzene selectivity, e.g., 90%, is attained, whereupon the co-feed of selectivating agent is discontinued. This co-feeding of selectivating agent with the hydrocarbon feed is a type of "trimselectivation" or "in situ selectivation". Reaction conditions for this in situ selectivation step generally include a temperature of from about 350° C. to about 540° C. and a pressure of from about atmospheric to about 5000 psig. The reaction stream is fed to the system at a rate of from about 0.1 WHSV to about 20 WHSV. Hydrogen may be fed at a hydrogen to hydrocarbon molar ratio of from about 0.1 to about 20.

The selectivating agent for trim-selectivation may be selected from among the exemplary silicon compounds discussed in greater detail above with respect to ex situ selectivation. Such compounds are referred to in this context as "trim-selectivating agents." For example, organic silicon compounds such as phenylmethyl silicone, dimethyl silicone, and mixtures thereof are suitable. According to one embodiment of the present invention, a silicone, containing phenylmethyl-silicone and dimethylsilicone groups in a ratio of about 1:1, is co-fed to the system, while the other components, e.g., hydrocarbon (with or without hydrogen), are fed in the amounts set forth above. The trim-selectivating agent is co-fed in an amount of from about 0.001 wt.% to about 10 wt.% of the hydrocarbon according to this preferred embodiment. Depending upon the percentage of selectivating agent used, the trim-selectivation will last for at least one hour, preferably about 1 to about 48 hours, most preferably less than 24 hours.

In this scheme the silicon compound will decompose to deposit additional silica to on the catalyst. During the in situ selectivating procedure the selectivity of the catalyst will be observed to increase further. The silicon-containing polymer or molecular species may be dissolved in toluene or other appropriate aromatic or hydrocarbon carrier. Preferably, the organic carrier for trim-selectivation is the hydrocarbon which is to be converted in the aromatization process.

Alternatively, the catalyst, prior to contacting with hydrocarbon under aromatization conditions, may be subjected to a trim-selectivation process known as "coke trimming". This process involves exposing the modified catalyst to a thermally decomposable organic compound at an elevated temperature in excess of the decomposition temperature of said compound but below the temperature at which crystallinity of the zeolite is adversely affected. Generally, this temperature will be less than about 650° C.

Organic materials, thermally decomposable under the above temperature conditions to provide coke trimming, encompass a wide variety of compounds including by way of example, hydrocarbons, such as paraffinic, cycloparaffinic, olefinic, cycloolefinic and aromatic; oxygen-containing organic compounds such as alcohols, aldehydes, ethers, ketones and phenols; heterocyclics such as furans, thiophenes, pyrroles and pyridines. Usually, it is contemplated that a thermally decomposable hydrocarbon, such as an olefin or paraffin, will be the source of coke, most preferably the olefin or paraffin itself being subjected to aromatization. In the latter case, the hydrocarbon is initially brought into contact with the catalyst under conditions of temperature and hydrogen concentration amenable to rapid coke formation. Typically, coke trimming is conducted at conditions outside the operating parameters used during the main time span of the catalytic cycle. When the desired coke deposition has been effected, the hydrocarbon feed is continued in contact with the coke-containing catalyst under conditions of temperature and hydrogen concentration conducive to aromatization, with a greatly reduced coking rate.

AROMATIZATION OF OLEFINS AND PARAFFINS

The modified zeolite catalysts useful in the present invention are advantageously used in the aromatization of hydrocarbon compounds to provide alkyl-substituted benzene products including xylenes which are highly enriched in the para-dialkyl substituted benzene isomer. The products of the aromatization process of the invention also show reduced amounts of polyalkylaromatic compounds, such as tri- and tetra-alkyaromatic compounds. Moreover, it has been found that the rate of coking or hydrocarbon deposition on the catalyst is reduced, thereby extending the life of the catalyst.

The hydrocarbon aromatizations of the invention include the use of the modified catalytic molecular sieves of the invention in a variety of conditions. Such process conditions are described, for example, in U.S. Pat. Nos. 5,019,263, 4,590,321, 4,326,994, 4,117,026, 3,760,024, and 3,756,942, the disclosures of which are incorporated herein by reference.

In general, catalytic conversion conditions over a catalyst comprising a modified zeolite include a temperature of from about 100° C. to about 760 C., a pressure of from about 0.1 atmosphere (bar) to about 200 atmospheres (bar), a weight hourly space velocity of from about 0 08 $hr^{-1}$ to about 2000 $hr^{-1}$ and a hydrogen/organic, e.g., hydrocarbon compound, mole ratio ($H_2$/HC) of from 0 to about 100.

Operating conditions employed in the process of the present invention will affect the xylene para-selectivity and hydrocarbon conversion. Such conditions include the temperature, pressure, space Velocity, molar ratio of the reactants, and the hydrogen to hydrocarbon mole ratio ($H_2$/HC). It has also been observed that an increased space velocity (WHSV) can enhance the para-selectivity of the modified catalyst in alkylbenzene disproportionation reactions. This characteristic of the modified catalyst allows for substantially improved throughput when compared to current commercial practices. In addition, it has been observed that the disproportionation process may be performed using $H_2$ as a diluent, thereby dramatically increasing the cycle length of the catalyst. For example, it has been observed that an increase in temperature can increase the activity of the modified catalyst.

A catalytic molecular sieve selectivated according to the invention may be contacted with a hydrocarbon feedstock under conditions for effecting vapor-phase aromatization. Conditions effective for accomplishing the high para-xylene selectivity and acceptable hydrocarbon conversion rates include a reactor inlet temperature of from about 200° C. to about 600° C., preferably from 350 C. to about 540 C.; a pressure of from about atmospheric to about 5000 psia, preferably from about 100 psia to about 1000 psia; a WHSV of from about 0.1 $hr^{-1}$ to about 20 $hr^{-1}$, preferably from about 2 $hr^{-1}$ to about 10 $hr^{-1}$; and a $H_2$/HC mole ratio of from about 0.1 to about 20, preferably from about 2 to about 6.

As used herein, the term "para-selectivity" means the proportion of the para-dialkyl-substituted benzene product, indicated as a percentage, among all of the dialkyl-substituted products, i.e., para-dialkyl; ortho-dialkyl; and meta-dialkylsubstituted products. Those skilled in the art will appreciate that, in many cases, the relative proximity of the boiling points of these isomers necessitates relatively expensive separation processes for the isolation of the para-substituted product. On the other hand, the para-substituted product is usually more readily separated from other components in the product stream such as benzene, toluene, and other $C_6$–$C_8$ and $C_9$+products.

The present invention is described in detail below in relation to the aromatization of hydrocarbons, such as propene, over a multiply-selectivated catalyst. Normally a single pass conversion of a hydrocarbon stream results in a product stream which includes $C_6$–$C_8$ aromatics such as benzene, toluene, mixed xylenes and $C_8$ aromatics as well as a variety of $C_{9+}$aromatics. In conventional processes, on the other hand, the content of the desired p-xylene does not normally exceed that of an equilibrium mixture of xylenes, i.e., about 24% p-xylene. Also, the product stream produced by conventional processes generally carries an unacceptably high $C_{9+}$content.

It is known in the art that the selectivity features of para-selective catalysts are dependent upon an interplay of catalytic reaction and mass transfer. This interaction is described by classical diffusion equations. Two catalyst properties, diffusion time and catalytic activity, are generally sufficient to characterize the shape selectivity of a catalyst, both with respect to its primary product distribution and its products at higher degrees of conversion. See, e.g., Olson et al., "Structure-Selectivity Relationship in *Xylene Isomerization and Selective Toluene Disproportionation*", *Catalytic Materials: Relationship Between Structure and Reactivity*, ACS Symposium Ser. No. 248 (1984). Similar considerations apply to the selective production of para-xylene from hydrocarbon aromatization. A catalyst treated in the manner described herein exhibits a desirable decreased ortho-xylene sorption rate parameter and therefore yields a significantly para-xylene enriched product from hydrocarbon aromatization.

As explained in greater detail elsewhere herein, the present invention provides a process for obtaining p-xylene at hydrocarbon conversions of at least 20%, preferably at least about 50%, with a p-xylene selectivity of greater than 85%, preferably at least 90%.

The hydrocarbon to be converted by the process of the invention includes one or more non-aromatic compounds selected from among $C_2$–$C_{12}$ alkanes, $C_2$–$C_{12}$ alkenes, $C_1$–$C_5$ alcohols, and mixtures thereof.

Saturated hydrocarbons capable of undergoing aromatization are suitable for use in the feed according to the process of the present invention. The feed can comprise one or more light saturated hydrocarbons having 2–12 carbon atoms preferably 2–7 carbon atoms. The light hydrocarbons may be branched or unbranched. Preferred light hydrocarbons include ethane, propane and butane.

It is preferable to avoid converting hydrocarbons having more than 5 carbon atoms directly to aromatic compounds. Instead, it is more convenient to crack such hydrocarbons and to convert the resulting lighter hydrocarbons to aromatic compounds in accordance with the present invention.

The feed may comprise saturated hydrocarbons, unsaturated hydrocarbons and/or non-aromatizable components, such as, for example, hydrogen, nitrogen and carbon dioxide. The amount of saturated hydrocarbons in the feed is not critical, although for economic reasons it is preferred for the feed to contain at least 1% saturated hydrocarbons. More preferably, the feed comprises at least 50% saturated hydrocarbons. Unsaturated hydrocarbons are especially desirable, since they are also converted to aromatic compounds. Preferred light unsaturated hydrocarbons include $C_2$–$C_{12}$ alkenes. More preferably the unsaturated hydrocarbons include $C_2$–$C_5$ alkenes. Such unsaturated compounds include propenes, butenes, or pentenes.

The hydrocarbon feed may include light non-aromatic alcohols. Preferred alcohols include $C_1$–$C_5$ alcohols, more preferably methanol and/or ethanol.

The hydrocarbon feed may also be dried, if desired, in a manner which will minimize moisture entering the reaction zone. Numerous methods known in the art are suitable for drying the hydrocarbon charge for the process of the invention. These methods include percolation through any suitable desiccant, for example, silica gel, activated alumina, molecular sieves or other suitable substances, or the use of liquid charge dryers.

This process may be conducted in either batch or fluid bed operation, with the attendant benefits of either operation readily obtainable. The effluent may be separated and distilled to remove the desired product, i.e., p-xylene, as well as other by-products. Alternatively, the $C_8$ fraction may be subjected to further separation, as in the case of xylenes, subjected to crystallization or the PAREX process to yield p-xylene.

In addition, the catalyst may be further modified in order to reduce the amount of undesirable by-products, particularly ethylbenzene. In order to avoid the need for downstream removal of heavier aromatics ($C_{9+}$) and other $C_8$ aromatics (e.g., ethylbenzene), the levels of these by-products are advantageously reduced by incorporating a hydrogenation/dehydrogenation function within the catalyst, such as by addition of a metal compound selected from Groups IB to VIII of the Periodic Table as described above.

The following Examples further illustrate the various features of the invention, and are not intended in any way to limit the scope of the invention, which is defined in the appended claims.

EXAMPLE 1

Modified catalyst was prepared via a multiple selectivation procedure according to the invention. The "parent" unmodified 65% HZSM-5/35% $SiO_2$ material having a calculated crystal size of 1.6 microns was subjected to three consecutive selectivation sequences. The first two selectivation sequences were each intended to add up to about 5 wt.% of silica to the catalyst. The third selectivation sequence was intended to add up to about 2.5 wt.% of silica to the catalyst. The detailed treatment is described below.

FIRST MODIFICATION 50.0 grams of HZSM-5/$SiO_2$ (1/16 inch extrudate, dried at 105° C.) was added to a solution of 4.6 grams of dimethylphenylmethyl polysiloxane (Dow-550) dissolved in 40 grams of dodecane. The catalyst was allowed to contact/absorb the silicone solution for several minutes, after which the dodecane was stripped under nitrogen at 210°–220° C. The catalyst was then placed in a metal box and calcined in a muffle furnace at 2° C./minute in a 80%/20% $N_2$/air mixture (60 cc/min total) to 538° C. The catalyst was held at 538° C. for about 4 hours. After cooling under $N_2$ the silica-modified catalyst was found to have gained 2.6 wt.%.

SECOND MODIFICATION 50.4 grams of the once-modified catalyst was added to a solution of 4.6 grams of dimethyl-phenylmethyl polysiloxane (Dow-550) dissolved in 40 grams of dodecane. The catalyst was allowed to contact/absorb the silicone solution for several minutes, after which the dodecane was stripped under nitrogen at 210–220 C. The catalyst was then placed in a metal box and calcined in a muffle furnace at 2 C./minute in a 80%/20% $N_2$/air mixture (60 cc/min total) to 538° C. The catalyst was held at 538° C. for about 4 hours. After cooling under $N_2$ the silica-modified catalyst was found to have gained 3.2 wt.%.

THIRD MODIFICATION 51.0 grams of the twice-modified catalyst was added to a solution of 2.4 grams of dimethylphenylmethyl polysiloxane (Dow-550) dissolved in 40 grams of dodecane. The catalyst was allowed to contact/absorb the silicone solution for several minutes, after which the dodecane was stripped under nitrogen at 210–220° C. The catalyst was then placed in a metal box and calcined in a muffle furnace at 2° C./minute in a 80%/20% $N_2$/air mixture (60 cc/min total) to 538° C. The catalyst was held at 538 C. for about 4 hours. After cooling under $N_2$ the silica-modified catalyst was found to have gained 2.1 wt.%.

Thus, after three treatments the catalyst had gained about 8.0 wt.% as silica.

EXAMPLE 2

To determine the comparative activity and selectivity of the modified and unmodified catalysts of Example 1, toluene disproportionation runs were conducted in automated units with on line gas chromatograph sampling. For each catalyst, approximately one gram of the modified catalysts was loaded into a stainless steel tube reactor, 0.25 inch in diameter. The sample was heated to reaction temperature at a heating rate of 2.0/min. The feed was alumina-percolated toluene.

TABLE 1

Ex Situ Selectivation Results

|  | Single Modified | Double Modified | Triple Modified | |
|---|---|---|---|---|
| Reaction Conditions |  |  |  |  |
| Temperature (°C.) | 465 | 465 | 465 | 485 |
| $H_2$/HC | 2 | 2 | 2 | 2 |
| Pressure (psig) | 500 | 500 | 500 | 500 |
| WHSV ($hr^{-1}$) | 3 | 3 | 3 | 3 |
| Toluene Conversion (Wt. %) | 37 | 22 | 14 | 24 |
| Product Yields (Wt. %) |  |  |  |  |
| $C_{5-}$ | 1.5 | 0.9 | 0.4 | 1.3 |
| Benzene | 16.2 | 8.3 | 6.0 | 10.6 |
| Ethylbenzene | 0.3 | 0.2 | 0.1 | 0.4 |
| Xylenes | 19.0 | 10.7 | 7.5 | 11.1 |
| Para-Xylene | 5.4 | 8.3 | 7.2 | 10.3 |
| Para-Selectivity | 28 | 78 | 95 | 93 |
| Benzene/Xylene Molar Ratio | 1.2 | 1.2 | 1.1 | 1.3 |

The data in Table 1 show that the selectivation proceeds in a step-wise manner, e.g., each successive treatment results in an increase in para-selectivity. In the second and third treatments, para-selectivity is much higher than that observed in an unselectivated catalyst. When using conventional untreated catalysts at these conversion levels, xylene proportions are similar to those obtained in an equilibrium mixture of xylenes, i.e., about 26% para-xylene. Raising the temperature of the triply treated catalyst from 465° C. to 485 C. increases toluene conversion to near the 25% level, however para-selectivity is still very high, i.e., >90%.

EXAMPLE 3

Properie aromatizations were conducted at 550° C. and atmospheric pressure, and 0.38 WHSV, using 1 g samples of two catalysts. For comparison purposes, the parent silica-bound 65% HZSM-5 catalyst (unmodified) employed in Example 1, and its silica-selectivated analog, i.e., catalyst selectivated three times as described in Example 1, were evaluated under identical reaction conditions. Reactions were performed using a ⅜" stainless steel reactor packed with one gram of catalyst. Reaction conditions included a temperature of 550° C. a weight hourly space velocity of 0.38 $hr^{-1}$ at atmospheric pressure. The reactor effluents were collected at 0° C. and analyzed by on-line gas chromatography. The results of this comparison are summarized in Table 2.

TABLE 2

|  | Unmodified | | Triple-Selectivated | |
|---|---|---|---|---|
|  | 7 Hours | 25 Hours | 7 Hours | 25 Hours |
| Methane | 5.58% | 1.34% | 5.68% | 3.97% |
| Ethane | 8.18% | 2.04% | 5.65% | 3.75% |
| Propane | 18.04% | 9.93% | 14.92% | 7.77% |
| Propene | 3.27% | 23.17% | 6.18% | 17.91% |
| Benzene | 11.45% | 2.38% | 11.97% | 5.63% |
| Toluene | 23.61% | 7.69% | 30.43% | 17.91% |
| Ethylbenzene | 0.85% | 0.87% | 1.38% | 1.61% |
| Xylenes | 13.95% | 7.37% | 7.30% | 9.67% |
| $C_{9+}$ Aromatics | 6.99% | 4.69% | 2.34% | 1.82% |
| Para-Xylene Selectivity (Avg.) |  | 28.1% |  | 94.6% |

After 7 hours on stream, the silica-selectivated catalyst yielded 51.15 wt.% $C_{6-C8}$ aromatics (consisting of 11.97% benzene, 30.43% toluene, and 8.75% xylenes and other $C_8$ aromatics) together with 1.82% $C_{9+}$ aromatics.

The xylenes produced by the selectivated catalyst throughout the reaction were significantly enriched in the para-isomer. Average analysis of liquids collected indicated the isomeric distribution of the xylenes to be 94.6% para-, 4.3% meta-, and 1.1% ortho-. No such preferential formation of para-xylene was observed for the unselectivated catalyst. A near equilibrium mixture of xylenes was produced, in which the para- isomer constituted only 28.1%

Figure 1:
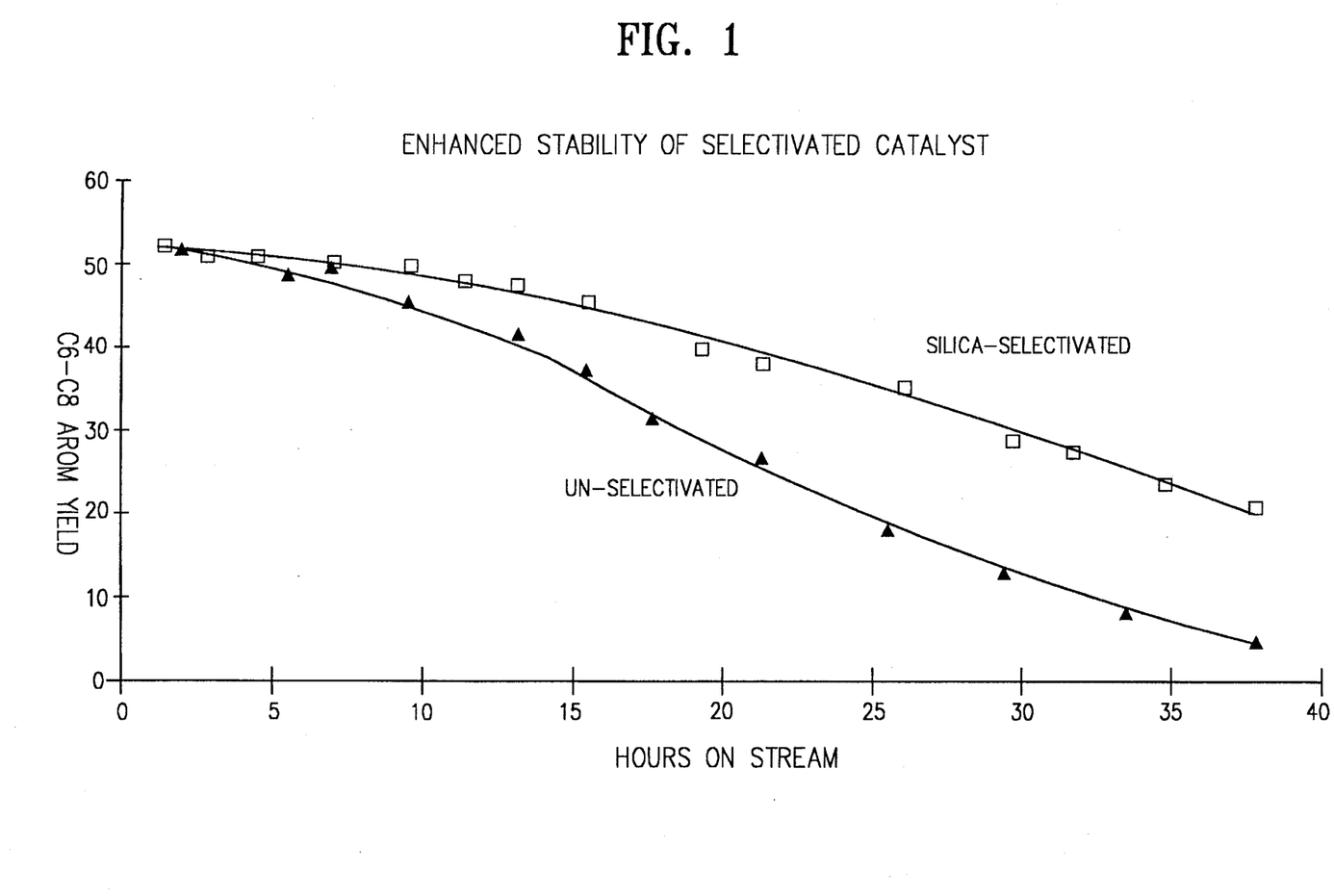
FIG. 1 illustrates the yield of $C_6$–$C_8$ aromatic compounds as a weight percentage of all products from an aromatization reaction catalyzed by a silica-selectivated catalyst of the invention as compared to an un-selectivated catalyst, as a function of duration of reaction.

The unselectivated catalyst, at 7 hours on stream, yielded 49.91% $C_6$–$C_8$ aromatics (consisting of 11.45% benzene, 23.61% toluene, and 14.85% xylenes and other $C_8$ aromatics), together with 7.0% $C_{9+}$ aromatics. At 25 hours on stream, the yield of $C_6$–$C_8$ aromatics declined to 18.3% (2.4% benzene, 7.7% toluene, and 8.2% $C_8$ aromatics). The unselectivated catalyst produced significantly more high boiling $C_{9+}$ aromatics and aged more rapidly (as shown in FIG. 1).

Analysis of the liquid product collected from the unselectivated HZSM-5 catalyst indicated a near-equilibrium distribution of xylene isomers, with 28.1% para-, 49.1% meta-, and 22.7% ortho-xylene produced. In contrast, the xylenes formed over the silica-selectivated catalyst were highly enriched in the para-isomer, with the para-selectivity averaging 94.6% (with 4.3% meta- and 1.1% ortho-).

Furthermore, formation of high-boiling $C_{9+}$ aromatic hydrocarbons was reduced over the selectivated catalyst by better than 60%.

Extensive catalyst aging was observed over a period of 30–40 hours, as expected for an aromatization process. Propene conversion declined from 96.7% at 7 hours on stream (HOS) to 53.4% by 37 HOS over the unselectivated HZSM-5, while the decline over the selectivated catalyst was from 93.8% propene conversion to 72.9% over the same time period. The lower aging rate observed for the selectivated catalyst is consistent with the lower production of $C_{9+}$ aromatics. (See FIG. 1.)

Use of a selectivated HZSM-5 catalyst in light paraffin and olefin aromatizations therefore improves product slates by reducing formation of high-boiling $C_{9+}$ aromatics while producing xylenes rich in the para- isomer.

EXAMPLE 4

The triply-selectivated catalyst prepared in Example 1, supra, was converted to a catalyst containing 1 wt.% gallium by impregnating 5 grams of the selectivated catalyst with 183 mg. gallium nitrate dissolved in 10 mL water. The catalyst was then dried in a rotovap and a vacuum oven.

The addition of 1 wt.% gallium to the catalyst increased the observed yield of aromatics from propene, as shown in Table 3, below.

TABLE 3

Effect of Gallium Addition to Selectivated HZSM-5
Reaction Conditions: 550° C., 0.38 WHSV, 3 HOS

| Product (Wt. %) | Sel. HZSM-5 | Ga/Sel. HZSM-5 |
|---|---|---|
| Ethane | 6.58% | 7.14% |
| Propane | 17.39% | 10.72% |
| Propene | 5.03% | 3.90% |
| Butanes | 3.40% | 2.46% |
| Benzene | 14.49% | 15.38% |
| Toluene | 30.80% | 34.06% |
| Ethylbenzene | 1.23% | 1.23% |
| Xylenes | 5.57% | 11.36% |
| $C_{9+}$ Aromatics | 2.31% | 3.31% |

The increase in benzene, toluene, and xylene (BTX) formation, from 50.86% to 60.8%, due to gallium is largely attributable to reduction in light paraffin production, especially propane. This effect of gallium has been demonstrated for other aromatization processes (e.g., U.S. Pat. No. 4,180,689), and is most significant in paraffin aromatizations.

The Ga-containing selectivated catalyst produced significantly more xylenes, with a maximum yield of 12.9% observed at 7 HOS. Analysis of the liquid product collected for the entire run indicated a para-xylene isomer selectivity of 87.5%.

EXAMPLE 5

The silica selectivated catalyst of Example 1 was used for the conversion of hydrotreated $C_6$–$C_7$ naphtha to aromatics in accordance with the invention. At 500° C., 0.7 WHSV, and atmospheric pressure, a net increase in aromatics of almost 30 wt.% was observed. During the first 6 hours on stream, virtually complete (>98%) conversion of n-hexane and n-heptane was observed. During the next 12 hours, gradual aging was observed as the n-hexane conversion decreased to 83%, while that of n-heptane declined to 92%.

Table 4, below, compares the composition of the naphtha feed ("Feed") and the aromatized naphtha effluent ("Product") after 10 hours on stream:

TABLE 4

Product Distribution from Aromatization of
Light Straight Run (LSR) Naphtha Over Selectivated HZSM-5
Reaction Conditions: 550° C., 0.7 WHSV, 1 atm, 10 HOS

| Component | Product (Wt. %) | Feed (Wt. %) |
|---|---|---|
| Methane + Ethane | 12.0% | 0 |
| Propane | 13.3% | 0 |
| Butanes | 5.0% | 0 |
| Total $C_1$–$C_4$ | 46.5% | 0 |
| Benzene | 10.2% | 2.1% |
| Toluene | 18.7% | 3.0% |
| Ethylbenzene | 1.2% | 0 |
| Xylenes | 4.6% | 0 |
| $C_{9+}$ | 1.3% | 0 |
| n-Hexane | 1.0% | 24.2% |
| n-Heptane | 0.2% | 16.2% |
| Para-Selectivity | 96.2% | — |

Analyses of the liquid products collected over a period of 18 hours indicated a very high para-xylene selectivity, which averaged 96.2% para-, 3.1% meta-, and 0.7% ortho-xylene.

The shape-selective cracking properties of the silicaselectivated HZSM-5 catalyst were quite apparent during the aromatization of the $C_6$–$C_7$ naphtha. The relative conversions of a few selected components (average of 3 samples) are shown in Table 5, below:

TABLE 5

Shape-Selective Cracking of Naphtha Components
Reaction Conditions: 550° C., 1.4 WHSV, 1 Atm., 20–23 HOS

| Component | % Converted |
|---|---|
| n-Hexane | 65% |
| n-Heptane | 80% |
| 3-Methylpentane | 67% |
| Cyclohexane | 15% |
| Methylcyclohexane | 5% |
| 3-Ethylpentane | 0% |

The greater conversion of n-heptane relative to n-hexane is a combination of the greater intrinsic cracking rate of heptane and the increased sorption of the higher boiling compound. Interestingly, no significant conversion differences at 550° C. were observed for n-hexane and 3-methylpentane cracking, indicative of a Constraint Index of 1.0. A slight increase in molecular size, however, from 3-methylpentane to 3-ethylpentane, significantly affected the cracking rate. Virtually no conversion of the latter was observed under conditions where two thirds of the 3-methylpentane was converted. The relative rate of naphthenes conversion was also reduced over the selectivated catalyst. Only 5% methylcyclohexane conversion was observed under conditions where 80% of the n-heptane was converted.

In view of these high selectivities favoring cracking of linear and methyl-branched hydrocarbons relative to naphthenes, the silica-selectivated HZSM-5 catalyst may offer potential advantages as an additive for fluid catalytic cracking (FCC) or dewaxing processes.

EXAMPLE 6

The gallium impregnated catalyst of Example 4 was used for the conversion of hydrotreated highly paraffinic $C_6$–$C_7$ light naphtha to aromatics in accordance with the invention.

The addition of 1 wt.% gallium to the silica-selectivated HZSM-5 catalyst increased the observed yield of aromatics from Light Straight Run (LSR) naphtha. Table 6, below, compares the composition of the naphtha feed and the aromatized naphtha products of selectivated catalysts, with and without gallium addition, at comparable n-hexane conversion levels (94%). Times on stream vary due to the more rapid aging rate of the galliumcontaining catalyst.

TABLE 6

Effect of Gallium Addition to Selectivated HZSM-5
Reaction Conditions: 550° C., 0.7 WHSV, 1 Atm.

| Component | Naphtha Feed | Ga/Sel. HZSM-5 (2 HOS) | Sel. HZSM-5 (12 HOS) |
|---|---|---|---|
| $C_1$–$C_4$ Paraffins | 0.0 | 22.7 | 29.4 |
| $C_2$–$C_4$ Olefins | 0.0 | 14.6 | 17.9 |
| Me-pentanes | 17.2 | 2.2 | 1.3 |
| n-Hexane | 24.2 | 1.5 | 1.5 |
| n-Heptane | 16.2 | 0.4 | 0.2 |

TABLE 6-continued

Effect of Gallium Addition to Selectivated HZSM-5
Reaction Conditions: 550° C., 0.7 WHSV, 1 Atm.

| Component | Naphtha Feed | Ga/Sel. HZSM-5 (2 HOS) | Sel. HZSM-5 (12 HOS) |
|---|---|---|---|
| Benzene | 2.1 | 11.1 | 9.6 |
| Toluene | 3.0 | 22.6 | 17.7 |
| Et-benzene | 0.0 | 1.1 | 1.1 |
| Xylenes | 0.0 | 7.3 | 4.3 |
| $C_{9+}$ Aromatics | 0.0 | 2.0 | 0.8 |
| $C_{5+}$ | 100.0 | 62.7 | 52.7 |
| $C_{6-8}$ Aromatics | 5.1 | 42.1 | 32.7 |
| Para-Selectivity | — | 92.9 | 96.2 |

The increase in benzene, toluene, and xylene formation due to gallium coincides with a reduction in $C_4$. production, which, as is noted elsewhere herein, is a well-recognized effect in other aromatization reactions.

Analysis of the liquid product collected at high conversions indicated a very high para-isomer selectivity for the xylenes produced: 92.9% para-, 5.8% meta-, and 1.1% ortho-xylene.

While the invention has been described with reference to specific embodiments, it will be apparent that numerous variations, modifications, and alternative embodiments of the invention are possible, and accordingly all such variations, modifications, and alternative embodiments are to be regarded as being within the spirit and scope of the present invention as claimed.

What is claimed is:

1. A process for enhanced shape selective hydrocarbon conversion to aromatics, comprising:
   contacting a reaction stream comprising hydrocarbon to be converted, under aromatization conditions, with a catalytic molecular sieve which has been modified by being exposed to a series of at least two ex situ selectivation sequences,
   wherein each of the ex situ selectivation sequences includes the steps of:
   a) contacting the catalytic molecular sieve with a selectivating agent in an organic carrier; and
   b) subsequently calcining the contacted catalytic molecular sieve.

2. The process of claim 1, wherein the aromatization conditions comprise a temperature of from about 100° C. to about 760° C., a pressure of from about 0.1 atmosphere to about 200 atmospheres, and a weight hourly space velocity of from about 0.08 to about 2000.

3. The process of claim 1, wherein the aromatization conditions further comprise a hydrogen/hydrocarbon mole ratio of from greater than 0 to about 100.

4. The process of claim 1, wherein the hydrocarbon to be converted comprises one or more non-aromatic compounds selected from the group consisting of $C_2$–$C_{12}$ alkanes, $C_2$–$C_{12}$ alkenes, $C_1$–$C_5$ alcohols, and mixtures thereof.

5. The process of claim 1, wherein the hydrocarbon to be converted comprises one or more non-aromatic compounds selected from the group consisting of $C_2$–$C_7$ alkanes.

6. The process of claim 1, wherein the hydrocarbon to be converted comprises one or more non-aromatic compounds selected from the group consisting of $C_2$–$C_5$ alkenes.

7. The process of claim 1, wherein the hydrocarbon to be converted comprises one or more non-aromatic compounds selected from the group consisting of methanol and ethanol.

8. The process of claim 1, wherein the catalytic molecular sieve has been modified by a series of between two and six ex situ selectivation sequences.

9. The process of claim 1, wherein the selectivating agent is selected from the group consisting of silicones, silicone polymers, silanes, and alkoxysilanes.

10. The process of claim 9, wherein the silicones and silicone polymers are selected from the group consisting of wherein $R_1$ and $R_2$ are independently selected from the group consisting of hydrogen, halogen, hydroxyl, alkyl, alkoxy, halogenated alkyl, aryl, halogenated aryl, aralkyl, halogenated aralkyl, alkaryl, and halogenated alkaryl, and n is between 2 and 1000; and wherein the silanes and alkoxysilanes are selected from the group consisting of wherein $R_3$, $R_4$, $R_5$ and $R_6$ are independently selected from the group consisting of hydrogen, halogen, hydroxyl, alkyl, alkoxy, halogenated alkyl, aryl, halogenated aryl, aralkyl, halogenated aralkyl, alkaryl, and halogenated alkaryl.

11. The process of claim 9, wherein the selectivating agent comprises dimethylphenylmethyl polysiloxane.

12. The process of claim 1, wherein the organic carrier comprises a linear, branched, or cyclic hydrocarbon.

13. The process of claim 12, wherein the organic carrier comprises dodecane.

14. The process of claim 1, wherein the catalytic molecular sieve comprises a zeolite having a Constraint Index of from about 1 to about 12 prior to selectivation.

15. The process of claim 1, wherein the catalytic molecular sieve contains an ion selected from the group consisting of hydrogen, hydrogen precursor, organic cations, and combinations thereof.

16. The process of claim 15, wherein the catalytic molecular sieve is modified in an as-synthesized condition.

17. The process of claim 1, wherein the catalytic molecular sieve contains a metal selected from the group consisting of platinum, gallium, zinc, and mixtures thereof.

18. The process of claim 1, wherein the modified catalytic molecular sieve has been further modified by the step of trim-selectivating the modified catalytic molecular sieve.

19. The process of claim 18, wherein the trim-selectivating step comprises contacting the modified catalytic molecular sieve with a thermally decomposable organic compound selected from the group consisting of paraffins, cycloparaffins, olefins, cycloolefins, aromatics, alcohols, aldehydes, ethers, ketones, phenols, heterocyclics, and mixtures thereof at a temperature in excess of the decomposition temperature of the thermally decomposable organic compound.

20. The process of claim 19, wherein the thermally decomposable organic compound is selected from the group consisting of $C_2$–$C_{12}$ alkanes, $C_2$–$C_{12}$ alkenes, and $C_1$–$C_5$ alcohols.

21. The process of claim 18, wherein the trim-selectivating step comprises contacting the modified catalytic molecular sieve with a reaction stream comprising hydrocarbon and a trim-selectivating agent.

* * * * *